United States Patent [19]

Dobson et al.

[11] Patent Number: 5,280,045
[45] Date of Patent: Jan. 18, 1994

[54] 4-(3,5-BIS(1,1-DIMETHYLETHYL-4-HYDROXYPHENYL)-4-OXOBUTANAMIDE COMPOUND USEFUL AS AN ANTI-INFLAMMATORY AGENT

[75] Inventors: Roy L. M. Dobson, Hamilton; Kenneth R. Wehmeyer, Cincinnati; Steven P. Sirko, Fairfield; Benjamin F. Floyd, Cincinnati, all of Ohio

[73] Assignee: The Procter & Gamble Company, Cincinnati, Ohio

[21] Appl. No.: 951,547

[22] Filed: Oct. 1, 1992

Related U.S. Application Data

[63] Continuation-in-part of Ser. No. 777,855, Oct. 16, 1991, abandoned.

[51] Int. Cl.$^5$ .................. A61K 31/135; A61K 31/165; C07C 59/74; C07C 229/00
[52] U.S. Cl. ....................... 514/621; 514/649; 562/459; 562/443; 564/167
[58] Field of Search ............ 514/568, 683, 684, 570, 514/621, 649; 562/459, 443; 564/167

[56] References Cited

U.S. PATENT DOCUMENTS

| | | | |
|---|---|---|---|
| 3,784,701 | 1/1974 | Tomcufcik et al. | 424/317 |
| 4,008,323 | 2/1977 | Cousse et al. | 514/570 |
| 4,130,666 | 12/1978 | Moore | 424/331 |
| 4,493,823 | 1/1985 | Möller et al. | 514/570 |
| 4,500,731 | 2/1985 | Bianchi et al. | 514/452 |
| 4,708,966 | 11/1987 | Loomans et al. | 514/689 |
| 4,714,776 | 12/1987 | Bell et al. | 562/460 |
| 4,968,710 | 11/1990 | Rustad | 514/381 |

FOREIGN PATENT DOCUMENTS

80/15460  2/1980  Japan .

OTHER PUBLICATIONS

Portnykh, N. V., A. A. Volod'kin & V. V. Ershov, "New Functional Derivatives of Sterically Hindered Phenols", Izv. Akad, Nauk, SSSR, Ser. Khim., vol. 4 (Apr., 1968), pp. 920–922.
C.A. 81 (1): 3608n–Andreas (1974).
C.A. 73 (11): 55826m–Engelhardt et al. (1970).
Berger; Alfred; Medicinal Chemistry, Third Edition Part 1 (1970) p. 75.
Dreher, E.-L., J. Bracht, M. El-Mobayed, P. Hutter, W. Winter & A. Rieker, "Synthese und Struktur von 7-tert-Butyl-2-methylbenzoxazolen", Chem. Ber., vol. 115 (1982), pp. 288–308.

*Primary Examiner*—Frederick E. Waddell
*Assistant Examiner*—T. J. Criares
*Attorney, Agent, or Firm*—Milton B. Graff, IV; David L. Suter; Ronald L. Hemingway

[57] ABSTRACT

The subject invention involves compositions comprising 4-(3,5-bis(1,1-dimethylethyl-4-hydroxyphenyl)-4-oxobutanamide, or 4-(3,5-bis-(1,1-dimethylethyl)-4-hydroxyphenyl)-4-oxobutanoic acid and pharmaceutically-acceptable salts thereof, and a pharmaceutically-acceptable carrier. The subject invention also involves methods for treating diseases characterized by inflammation and/or pain, such as rheumatoid arthritis and osteoarthritis, in humans or lower animals by administration of a safe and effective amount of this compound to the human or lower animal in need of such treatment.

10 Claims, No Drawings

4-(3,5-BIS(1,1-DIMETHYLETHYL-4-HYDROXYPHENYL)-4-OXOBUTANAMIDE COMPOUND USEFUL AS AN ANTI-INFLAMMATORY AGENT

This is a continuation-in-part of application Ser. No. 07/777,855, filed on Oct. 16, 1991 now abandoned.

TECHNICAL FIELD

The subject invention relates to nonsteroidal anti-inflammatory drugs, particularly to substituted di-tert-butylphenol compounds.

BACKGROUND OF THE INVENTION

Certain di-tert-butylphenol compounds and other compounds structurally related thereto have been found to have significant anti-inflammatory and/or analgesic activity. Such compounds are disclosed in the following references: U.S. Pat. No. 3,784,701 issued to Tomcufcik, Grassing & Sloboda on Jan. 8, 1974; U.S. Pat. No. 4,124,725 issued to Moore on Nov. 7, 1978; U.S. Pat. No. 4,130,666 issued to Moore on Dec. 19, 1978; U.S. Pat. No. 4,535,165 issued to Moore on Aug. 13, 1985; U.S. Pat. No. 4,636,516 issued to Kubo, Isomura, Sakamoto & Homma on Jan. 13, 1987; U.S. Pat. No. 4,677,113 issued to Bell & Moore on Jun. 30, 1987; U.S. Pat. No. 4,708,966 issued to Loomans, Matthews & Miller on Nov. 24, 1987; U.S. Pat. No. 4,714,776 issued to Bell & Moore on Dec. 22, 1987; U.S. Pat. No. 4,968,710 issued to Rustad on Nov. 6, 1990; EPO Patent Application No. 0,211,670 of Panetta (Eli Lilly & Company), published Feb. 25, 1987; EPO Patent Application No. 0,286,364 of Scherrer & Rustad (Riker Laboratories, Inc.), published Oct. 12, 1988; Japanese Patent No. 80/15,460 of Noda, Nakagawa, Hirano, Tsuji & Ide (Jpn. Kokai, Tokkyo Koho), published Feb. 2, 1980; Hidaka, Hosoe, Ariki, Takeo, Yamashita, Katsumi, Kondo, Yamashita & Watanabe, "Pharmacological Properties of a New Anti-inflammatory Compound, a(3,5-di-tertbutyl-4-hydroxybenzylidene)-g-butyrolactone (KME-4), and its Inhibitory Effects on Prostaglandin Synthetase and 5-lipoxygenase", *Jpn. J. Pharmacol*, Vol. 36, No. 1 (1984), pp. 77–85; and VanDerGoot, H., J. C. Eriks, P. J. VanRhijn-VanDerSchaar, O. P. Zuiderveld & W. T. Nauta, "The Synthesis and Antiinflammatory Activity of Substituted 2-4-Hydroxyphenyl-1,3-indandiones", *European Journal of Medicinal Chemistry*, Vol. 13, No. 5 (1978), pp. 425–428.

Although a number of di-tert-butylphenol compounds have been demonstrated to exhibit anti-inflammatory activity, many such compounds exhibits little or no anti-inflammatory activity. The unpredictability of this property makes it necessary to screen each compound of the class to determine whether it possesses such activity.

It is an object of the subject invention to provide a compound which has effective anti-inflammatory, analgesic and/or anti-arthritic activity.

It is a further object of the subject invention to provide methods for treating inflammation, pain and/or arthritis using the compound.

SUMMARY OF THE INVENTION

The subject invention involves compositions comprising 4-(3,5-bis(1,1-dimethylethyl)-4-hydroxyphenyl)-4-oxobutanoic acid, and pharmaceutically-acceptable salts thereof, or 4-(3,5-bis(1,1-dimethylethyl)-4-hydroxyphenyl)-4-oxobutanamide, and a pharmaceutically-acceptable carrier. The subject invention also involves methods for treating diseases characterized by inflammation and/or pain, such as rheumatoid arthritis and osteoarthritis, in humans or lower animals by administration of a safe and effective amount of this compound to the human or lower animal in need of such treatment.

DETAILED DESCRIPTION OF THE INVENTION

The subject invention involves a particular di-tert-butylphenol compound having the following structure:

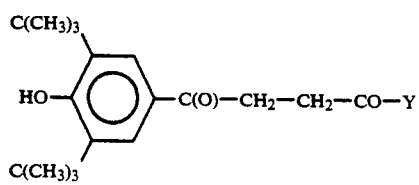

wherein —Y is —OH or —$NH_2$.

These compounds, 4-(3,5-bis(1,1-dimethylethyl)-4-hydroxyphenyl4-oxobutanoic acid and 4-(3,5-bis(1,1-dimethylethyl)-4-hydroxyphenyl-4-oxobutanamide (hereinafter the "acid Compound" and the "amide Compound", respectively, collectively the "Compounds"), and the pharmaceutically-acceptable salts of the acid Compound, have been found to be particularly useful anti-inflammatory agents.

The term "pharmaceutically-acceptable salts", as used herein, means the acid Compound in its salt forms which have the same general pharmacological properties as the protonated form of such Compound, and which are acceptable from a toxicity viewpoint. Pharmaceutically-acceptable salts include alkali metal (e.g., sodium and potassium), alkaline earth metal (e.g., calcium and magnesium), non-toxic heavy metal (e.g., stannous and indium), and ammonium and low molecular weight substituted ammonium (mono-, di- and trimethyl or ethyl ammonium) salts. Preferred are the sodium, potassium, and ammonium salts.

The acid Compound is disclosed as a starting material in "Dreher, E. L., J. Bracht, M. El-Mobayed, P. Huetter, W. Winter & A. Rieker, "Electrochemical Oxidation. VII. Synthesis and Structure of 7-tert-butyl-2-methylbenzoxazoles", *Chem. Ber.*, Vol. 115, No. 1 (1982), pp. 288–308. (See page 288, compound 1e). The acid Compound and a method for synthesizing it are disclosed in Portnykh, N.V., A. A. Volod'kin & V. V. Ershov, "New Functional Derivatives of Sterically Hindered Phenols", *Izv. Akad. Nauk, SSSR, Ser. Khim.*, Vol. 4 (April, 1968), pp. 920–922. The acid Compound is referred to therein as g-(4-hydroxy-3,5-di-tert-butyl phenyl)-g-ketobutyric acid.

The amide Compound is believed to be a novel compound.

In order to determine and assess pharmacological activity, testing of the Compounds in animals is carried out using various assays known to those skilled in the art. The anti-inflammatory activity of the Compounds can be conveniently demonstrated using an assay designed to test the ability of the Compounds to antagonize the local edema which is characteristic of the inflammatory response. Examples of such known tests include the rat carrageenan edema test, the oxazolone-induced inflamed mouse ear test, and the mouse arachadonic acid-induced inflamed ear test. Analgesic activity may be tested in art-known models such as the acetylcholine abdominal constriction model in mice, the Randall-Selitto model in rats, and the hot-plate test in mice or rats. Another useful art-known test is the rat adjuvant arthritis test which is a useful model for assessing anti-inflammatory activity, anti-arthritic and anti-resorptive activity in a chronic, rather than an acute, model.

These and other appropriate tests for pharmacological activity are disclosed and/or referred to in U.S. Pat. No. 4,130,666 issued to Moore on Dec. 19, 1978; U.S. Pat. No. 4,431,656 issued Feb. 14, 1984 to Katsumi, et al.; U.S. Pat. No. 4,440,784 issued to Katsumi, et al. on Apr. 3, 1984; Japanese Patent Application 85/54315 of Katsumi, et al., published Mar. 28, 1985; European Patent Application No. 0,059,090 of Yamanuchi Pharmaceutical Company Ltd., published Sep. 1, 1982; Opas, E. V., R. J. Bonney & J. L. Humes, "Prostaglandin and Leukotriene Synthesis in Mouse Ears Inflamed by Arachadonic Acid", *The Journal of Investigative Dermatology*, Vol. 84, No. 4 (1985), pp. 253-256; Swingle, K. F., R. L. Bell & G. G. I. Moore, "Anti-inflammatory Activity of Antioxidants", *Anti-inflammatory and Antirheumatic Drugs*, Vol. III, Chapter 4, K. D. Rainsford, ed., CRC Press, Inc., (1985), pp. 105-126; Adamkiewicz, V. W., W. B. Rice & J. D. McColl, "Antiphlogistic Effect of Trypsin in Normal and in Adrenalectomized Rats", *Canadian Journal of Biochemistry & Physiology*, Vol. 33 (1955), pp. 332-339; Sellye, H., "Further Studies Concerning the Participation of the Adrenal Cortex in the Pathogenesis of Arthritis", *British Medical Journal*, Vol. 2 (1949), pp. 1129-1135; and Winter, C. A., E. A. Risley & G. W. Nuss, "Carrageenin-Induced Edema in Hind Paw of the Rat as an Assay for Antiinflammatory Drugs" *Proceedings of Society of Experimental Biology and Medicine*, Vol. 111 (1962), pp. 544-547; the disclosure of all these references are incorporated herein by reference.

The Compounds can be synthesized using the following procedures:

solution is pink in color. During the course of the reaction, the solution develops a deep lilac color.

The reaction solution (temperature=27° C.) is poured into a separatory funnel containing $Et_2O$ (100 ml). The color goes to deep yellow. The solution is extracted two times with aqueous saturated $K_2CO_3$ solution, then saturated NaCl solution. The solution is dried over $MgSO_4$ and is concentrated in vacuo (using a rotary evaporator) to an oil that immediately solidifies. The crude material is dissolved in 90 ml hot hexane and allowed to cool, resulting in crystallization of slightly yellow needles which are separated from the supernatant by filtration. The crystals are washed twice with hexane and allowed to dry. The melting point of the resulting crystals of compound (1) above is 101°-103° C.

To a 100 ml round-bottom flask is charged compound (1) (1.6 gm, 5.0 mmol) and about 20 ml of methanol, stirring until compound (1) is dissolved. KOH (0.56 gm, 10 mmol) is added. The solution is heated with stirring to dissolve the KOH pellets. The solution is allowed to stir overnight.

The reaction solution is transferred to a 250 ml flask. The solvent is removed in vacuo. Using water and $CH_2Cl_2$, the resulting white solid is transferred to a conical flask; concentrated (12N) HCl is added; and the material is transferred to a separatory funnel. The material is washed two times with water, dried, and concentrated in vacuo. The concentrate is dissolved in hot hexane. The volume is reduced to about 25 mL in vacuo, and the solution is cooled, resulting in crystallization. The crystals of compound (2) above (the acid Compound) are separated from the supernatant by filtration. The crystals are washed twice with hexane and allowed to dry. The melting point of the resulting crystals of the acid Compound is 169.5°-174.0° C.

The acid Compound (2.0 g, 6.5 mmol) and N,N'-dicyclohexylcarbodiimide (1.6 g, 7.8 mmol) are added to a 100 mL round-bottom flask, and 20 mL of $CH_2Cl_2$ is added. The solution is cooled to 0° C., and an excess of

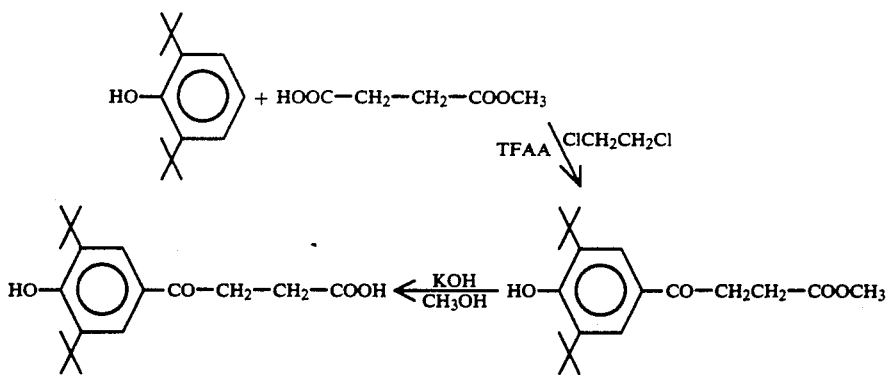

To a 50 ml 3-neck flask equipped with argon inlet and thermometer is charged 2,6-di-t-butylphenol (5.5 gm, 26.6 mmole) (Schenectady Chemical Co.), methyl hydrogen succinate (4.0 gm, 30.3 mmole) (Aldrich Chemical Company), and 1,2-dichloroethane. The mixture is stirred for 10 minutes; the resulting mixture is not quite homogeneous. The starting temperature is 23° C.; the mixture cools to 15° C. during stirring. Trifluoroacetic anhydride (TFAA) (3.76 ml, 5.59 gm, 26.6 mmol) (Aldrich Chemical Co.) is added all at once. The temperature rises to 29° C. After about 20 minutes, the clear ammonia (condensed by passing ammonia gas into $CH_2Cl_2$ cooled to $-78°$ C.) is added in one portion. 4-Dimethylaminopyridine (32 mg, 0.26 mmol) is added and the reaction is stirred for 30 minutes. The N,N'-dicyclohexylurea which forms is filtered off and the $CH_2Cl_2$ is washed with water and brine. The solution is dried over $MgSO_4$ and concentrated in vacuo. The crude product is triturated with hexane and then purified by silica gel flash chromatography with 5% MeOH in $CH_2Cl_2$ as eluant. Crystallization of the resulting product from 60/40 ethyl acetate/hexane gives off-white crystals of the amide Compound, having a melting point of 155°-156° C.

Compositions of the subject invention comprise a safe and effective amount of the Compounds, or a pharmaceutically-acceptable salt of the acid Compound, and a pharmaceutically-acceptable carrier. As used herein, "safe and effective amount" means an amount of a Compound sufficient to significantly induce a positive modification in the condition to be treated, but low enough to avoid serious side effects (at a reasonable benefit/risk ratio), within the scope of sound medical judgement. A safe and effective amount of a Compound will vary with the particular condition being treated, the age and physical condition of the patient being treated, the severity of the condition, the duration of the treatment, the nature of concurrent therapy, the particular pharmaceutically-acceptable carrier utilized, and like factors within the knowledge and expertise of the attending physician.

Compositions of the subject invention preferably comprise from about 0.1% to about 99.9% by weight of a Compound, more preferably from about 20% to about 80%, and most preferably from about 40% to about 70%.

In addition to the Compound, the compositions of the subject invention contain a pharmaceutically-acceptable carrier. The term "pharmaceutically-acceptable carrier", as used herein, means one or more compatible solid or liquid filler diluents or encapsulating substances which are suitable for administration to a human or lower animal. The term "compatible", as used herein, means that the components of the composition are capable of being commingled with the Compound, and with each other, in a manner such that there is no interaction which would substantially reduce the pharmaceutical efficacy of the composition under ordinary use situations. Pharmaceutically-acceptable carriers must, of course, be of sufficiently high purity and sufficiently low toxicity to render them suitable for administration to the human or lower animal being treated.

Some examples of substances which can serve as pharmaceutically-acceptable carriers or components thereof are sugars, such as lactose, glucose and sucrose; starches, such as cornstarch and potato starch; cellulose and its derivatives, such as sodium carboxymethyl cellulose, ethyl cellulose, cellulose acetate; powdered tragacanth; malt; gelatin; talc; solid lubricants, such as stearic acid, magnesium stearate; calcium sulfate; vegetable oils, such as peanut oil, cottonseed oil, sesame oil, olive oil, corn oil and oil of theobroma; polyols such as propylene glycol, glycerin, sorbitol, mannitol, and polyethylene glycol; algenic acid; emulsifiers, such as the Tweens®; wetting agents such as sodium lauryl sulfate; coloring agents; flavoring agents, excipients; tableting agents; stabilizers; antioxidants; preservatives; pyrrogen-free water; isotonic saline; and phosphate buffer solutions.

The choice of a pharmaceutically-acceptable carrier to be used in conjunction with a Compound is basically determined by the way the Compound is to be administered.

If the Compound is to be injected, the preferred pharmaceutically-acceptable carrier is sterile, physiological saline, with blood compatible suspending agent, the pH of which has been adjusted to about 7.4.

Suitable pharmaceutically-acceptable carriers for topical application include those suited for use in lotions, creams, gels and the like. Topical compositions preferably contain from about 1% to about 50% of an emollient.

The preferred mode of administering the Compound is orally. The preferred unit dosage form is therefore tablets, capsules and the like, comprising a safe and effective amount of the Compound, which is preferably from about 5 mg to about 3500 mg, more preferably from about 10 mg to about 1000 mg, and most preferably from about 25 mg to about 600 mg. The pharmaceutically-acceptable carriers suitable for the preparation of unit dosage forms for oral administration are well-known in the art. Their selection will depend on secondary considerations like taste, cost, and shelf stability, which are not critical for the purposes of the subject invention, and can be made without difficulty by a person skilled in the art.

Particularly preferred oral composition carriers suitable for compositions of the subject invention are disclosed in pending U.S. Patent application Ser. Nos. 07/732,951 of Kelm & Bruns, filed Jul. 19, 1991, entitled "Pharmaceutical Compositions of Tebufelone", and 07/885,932 of Kelm & Dobrozsi, filed May 19, 1992, entitled "Solid Dispersion Compositions of Tebufelone", hereby incorporated herein by reference.

Another aspect of the subject invention is methods for treating diseases characterized by inflammation by administering a safe and effective amount of a Compound to a human or lower animal in need of such treatment. The preferred mode of administration is oral, but other known methods of administration are contemplated as well, e.g., dermatomucosally (for example, dermally, rectally and the like) and perenterally (for example, by subcutaneous injection, intramuscular injection, intraarticular injection, intravenous injection and the like). Ocular administration and inhalation are also included. Thus specific modes of administration include, without limitation, oral, transdermal, mucosal, sublingual, intranasal, intramuscular, intravenous, intraperitoneal, subcutaneous and topical administration.

The term "diseases characterized by inflammation", as used herein, means conditions which are known to involve inflammation, such as arthritis (e.g., rheumatoid arthritis, osteoarthritis, psoriatic arthritis, juvenile arthritis, Reiter's syndrome, infectious arthritis, and ankylosing spondylitis, systemic lupus, erythematosus and gout), as well as the presence of inflammation whether or not it is associated with an identifiable disease. Diseases characterized by inflammation further include inflammation of the gastrointestinal tract, including the oral cavity (e.g., inflammation associated with gingivitis or periodontal disease) and bowels (e.g., inflammation associated with inflammatory Bowel Disease); inflammation associated with dermatological diseases (e.g., psoriasis); and inflammation associated with the respiratory tract (e.g., asthma, bronchitis).

Preferred doses of the Compounds range from about 0.2 mg/kg to about 70 mg/kg, more preferably from about 0.5 mg/kg to about 12 mg/kg. Such doses are preferably administered from about once to about six times daily, more preferably from about twice to about four times daily.

The following nonlimiting examples illustrate the subject invention.

EXAMPLE 1

Pharmaceutical compositions in the form of tablets are prepared by conventional methods, such as mixing and direct compaction, formulated as follows:

| Ingredient | Quantity (mb per tablet) |
| --- | --- |
| Amide Compound | 200 |
| Microcrystalline Cellulose | 100 |
| Sodium Starch Glycolate | 30 |
| Magnesium Stearate | 3 |

When administered orally two times daily, the above composition significantly reduces the inflammation in a patient suffering from rheumatoid arthritis. A significant benefit is also achieved by twice daily administration of this composition to a patient suffering from osteoarthritis.

EXAMPLE 2

A pharmaceutical composition in capsule form is prepared by conventional methods, formulated as follows:

| Ingredient | Quantity (mg per capsule) |
| --- | --- |
| Acid Compound | 200 |
| Lactose | To fill to volume of capsule |

The above capsule administered orally once a day substantially reduces the symptomology of a patient afflicted with rheumatoid arthritis or osteoarthritis.

While particular embodiments of the subject invention have been described, it would be obvious to those skilled in the art that various changes and modifications to the compositions disclosed herein can be made without departing from the spirit and scope of the invention. It is intended to cover, in the appended claims, all such modifications that are within the scope of this invention.

What is claimed is:

1. A compound 4-(3,5-bis(1,1-dimethylethyl-4-hydroxyphenyl)-4-oxobutanamide.

2. A pharmaceutical composition comprising:
   (a) a safe and effective amount of the compound 4-(3,5-bis(1,1-dimethylethyl-4-hydroxyphenyl)-4-oxobutanamide; and
   (b) a pharmaceutically-acceptable carrier.

3. A pharmaceutical composition in dosage unit form comprising:
   (a) from about 10 mg to about 3500 mg of the compound 4-(3,5-bis(1,1-dimethylethyl-4-hydroxyphenyl)-4-oxobutanamide; and
   (b) a pharmaceutically-acceptable carrier.

4. The composition of claim 3 wherein the dosage unit form comprises from about 5 mg to about 1000 mg of the compound.

5. The composition of claim 3 wherein the dosage form is a tablet or capsule comprising from about 10 mg to about 600 mg of the compound.

6. A method of treating inflammation by administering a safe and effective amount of the compound 4-(3,5-bis(1,1-dimethylethyl-4-hydroxyphenyl)-4-oxobutanamide to a human or lower animal in need of such treatment.

7. The method of claim 6 wherein the disease is rheumatoid arthritis.

8. The method of claim 6 wherein the disease is osteoarthritis.

9. The method of claim 6 wherein from about 0.2 mg/kg to about 70 mg/kg of the compound is administered from about 1 to about 6 times daily.

10. The method of claim 6 wherein from about 0.5 mg/kg to about 12 mg/kg of the compound is administered from about 1 to about 4 times daily.

* * * * *